US008926498B2

(12) United States Patent
Weng et al.

(10) Patent No.: US 8,926,498 B2

(45) Date of Patent: Jan. 6, 2015

(54) DEVICE FOR TREATMENT OF PREMATURE EJACULATION OR STIMULATION OF A MALE ORGAN

(76) Inventors: Hao Qi Weng, Hong Kong (HK); Ho Chuk Yung, Hong Kong (HK)

( * ) Notice: Subject to any disclaimer, the term of this patent is extended or adjusted under 35 U.S.C. 154(b) by 731 days.

(21) Appl. No.: 13/081,513

(22) Filed: Apr. 7, 2011

(65) Prior Publication Data

US 2012/0136203 A1 May 31, 2012

(30) Foreign Application Priority Data

Nov. 26, 2010 (CN) ...................... 2010 2 0627103 U

(51) Int. Cl.
*A61F 5/00* (2006.01)
*A61H 19/00* (2006.01)

(52) U.S. Cl.
CPC ........ *A61H 19/32* (2013.01); *A61H 2201/0153* (2013.01); *A61H 2201/0207* (2013.01); *A61H 2201/0214* (2013.01); *A61H 2201/0242* (2013.01); *A61H 2201/169* (2013.01)
USPC ............................................................ 600/38

(58) Field of Classification Search
CPC ......... A61H 5/00; A61H 19/00; A61H 19/32; A61B 10/0058; A61F 5/0096; A61D 19/00
USPC ...................................................... 600/38–41
See application file for complete search history.

(56) References Cited

U.S. PATENT DOCUMENTS

| | | | |
|---|---|---|---|
| 2,433,538 A | 12/1947 | Warner | |
| 5,782,818 A * | 7/1998 | Shubin | 604/349 |
| 5,807,360 A | 9/1998 | Shubin | |
| 2006/0235266 A1* | 10/2006 | Nan | 600/38 |
| 2008/0065033 A1* | 3/2008 | Matsuura | 604/349 |

FOREIGN PATENT DOCUMENTS

EP 1897519 A1 3/2008

OTHER PUBLICATIONS

Examination Report of European Patent Application No. 11165397.8.

* cited by examiner

*Primary Examiner* — Samuel Gilbert

(57) ABSTRACT

A device for treatment of premature ejaculation or stimulation of a male organ includes an elastic sleeve mounted within a housing, at least one aperture formed on the elastic sleeve, and at least one liquid-absorbing member held between the housing and the elastic sleeve over the at least one aperture. The at least one liquid-absorbing member is adapted to soak up a liquid with a temperature higher or lower than the body temperature of a user and deliver the liquid through the at least one aperture and into the elastic sleeve when the at least one liquid-absorbing member is squeezed by a male organ of the user frictionally moving to-and-fro inside the elastic sleeve, thereby stimulating the male organ and reducing the sensitivity thereof.

17 Claims, 8 Drawing Sheets

DEVICE FOR TREATMENT OF PREMATURE EJACULATION OR STIMULATION OF A MALE ORGAN

CROSS-REFERENCE TO RELATED APPLICATIONS

This application claims priority of Chinese Patent Application No. 201020627103.8 filed on Nov. 26, 2010, the entire content of which is hereby incorporated by reference.

FIELD OF THE TECHNOLOGY

The present application relates to a device for treatment of premature ejaculation or stimulation of a male organ.

BACKGROUND

Currently, there are various methods for the treatment of premature ejaculation. One method is drug treatment. Pills for the treatment of premature ejaculation can be taken 1-3 hours before sexual intercourse. However, drugs usually have side effects and may present risk to the health of some people.

Another method is the reduction of penile sensation. Reducing the sensitivity of the penis can prolong the time to ejaculation. Common techniques include the use of special condoms. However, one major drawback of the use of these special condoms is the loss of sensational feeling during sexual intercourse. Further, anesthetic creams or sprays can be applied directly to the head of the penis between 5 and 30 minutes before sexual intercourse. However, anesthetics can sometimes cause numbness of the penis and reduce pleasurable sensations during sexual intercourse.

There is a need to produce an improved device for the treatment of premature ejaculation that could alleviate the drawbacks of the existing methods.

The above description of the background is provided to aid in understanding the existing methods for treatment of premature ejaculation or stimulation of a male organ, but is not admitted to describe or constitute pertinent prior art to the device for treatment of premature ejaculation or stimulation of a male organ disclosed in the present application, or consider any cited documents as material to the patentability of the claims of the present application.

SUMMARY

According to one aspect, there is provided a device for treatment of premature ejaculation or stimulation of a male organ including a housing, an elastic sleeve mounted within the housing, at least one aperture formed on the elastic sleeve, and at least one liquid-absorbing member held between the housing and the elastic sleeve over the at least one aperture. The at least one liquid-absorbing member is adapted to soak up a liquid with a temperature higher or lower than the body temperature of a user and deliver the liquid through the at least one aperture and into the elastic sleeve when the at least one liquid-absorbing member is squeezed by a male organ of the user frictionally moving to-and-fro inside the elastic sleeve.

In one embodiment, the at least one liquid-absorbing member can be a foam member. The liquid may be a lubricant or water. The temperature of the liquid may be warm, hot, cold or ice-cold. The device may include a first plurality of apertures formed at one side of the elastic sleeve, and a second plurality of apertures formed at an opposite side of the elastic sleeve. An outer surface of the elastic sleeve can be integrally formed with a plurality of ribs extending longitudinally along and spaced circumferentially about the elastic sleeve, and the plurality of ribs is formed with cut-out portions defining a space for holding therein the at least one liquid-absorbing member. The device may include two liquid-absorbing members, wherein one liquid-absorbing member is held between the housing and one side of the elastic sleeve and is soaked with a warm/hot liquid, and the other liquid-absorbing member is held between the housing and an opposite side of the elastic sleeve and is soaked with a cold/ice-cold liquid, whereby rotation of the housing around the male organ 180 degrees clockwise or anticlockwise stimulates the male organ by alternate warm/hot and cold/ice-cold liquid.

In one embodiment, the housing may include two substantially semi-cylindrical housing parts detachably fastened together by fastening elements formed along longitudinal edges of the two housing parts. The fastening elements may include a plurality of resilient latches of generally L-shape cross section formed on the longitudinal edges of one of the two housing parts, and a plurality of latch-retaining recesses formed on inner surfaces of the longitudinal edges of the other one of the two housing parts for engagement with the latches respectively. The at least one liquid-absorbing member may be generally semi-annular or quarter-annular in shape. The device may further include a plurality of reinforcing extensions extending from the longitudinal edges of one of the two housing parts, and engageable with a plurality of inner surfaces along the longitudinal edges of the other one of the two housing parts respectively when the two housing parts are fastened together by the fastening elements. The device may further include two internally threaded end caps for closing two opposite externally threaded open ends of the housing respectively. The device may further include a threaded ring threadably engaged with and between each externally threaded open end of the housing and its corresponding internally threaded end cap.

According to another aspect, there is provided a device for treatment of premature ejaculation or stimulation of a male organ including an elastic sleeve, at least one aperture formed on the elastic sleeve, and at least one liquid-absorbing member held over the at least one aperture. The at least one liquid-absorbing member is adapted to soak up a liquid with a temperature higher or lower than the body temperature of a user and deliver the liquid through the at least one aperture and into the elastic sleeve when the at least one liquid-absorbing member is squeezed. In one embodiment, the at least one liquid-absorbing member can be a foam member. The liquid can be a lubricant or water. The temperature of the liquid may be warm, hot, cold or ice-cold. The device may have a first plurality of apertures formed at one side of the elastic sleeve, and a second plurality of apertures formed at an opposite side of the elastic sleeve. An outer surface of the elastic sleeve may be integrally formed with a plurality of ribs extending longitudinally along and spaced circumferentially about the elastic sleeve, and the plurality of ribs is formed with cut-out portions defining a space for holding therein the at least one liquid-absorbing member. The device may include two liquid-absorbing members, wherein one liquid-absorbing member is held at one side of the elastic sleeve and is soaked with a warm/hot liquid, and the other liquid-absorbing member is held at an opposite side of the elastic sleeve and is soaked with a cold/ice-cold liquid. The at least one liquid-absorbing member may be generally semi-annular or quarter-annular in shape.

Although the device for treatment of premature ejaculation or stimulation of a male organ disclosed in the present application is shown and described with respect to certain embodiments, it is obvious that equivalents and modifications will occur to others skilled in the art upon the reading and understanding of the specification. The present application includes all such equivalents and modifications, and is limited only by the scope of the claims.

BRIEF DESCRIPTION OF THE DRAWINGS

Specific embodiments of the device for treatment of premature ejaculation or stimulation of a male organ disclosed in the present application will now be described by way of example with reference to the accompanying drawings.

DETAILED DESCRIPTION

Reference will now be made in detail to a preferred embodiment of the device for treatment of premature ejaculation or stimulation of a male organ disclosed in the present application, examples of which are also provided in the following description. Exemplary embodiments of the device for treatment of premature ejaculation or stimulation of a male organ disclosed in the present application are described in detail, although it will be apparent to those skilled in the relevant art that some features that are not particularly important to an understanding of the device for treatment of premature ejaculation or stimulation of a male organ may not be shown for the sake of clarity.

Furthermore, it should be understood that the device for treatment of premature ejaculation or stimulation of a male organ disclosed in the present application is not limited to the precise embodiments described below and that various changes and modifications thereof may be effected by one skilled in the art without departing from the spirit or scope of the appended claims. For example, elements and/or features of different illustrative embodiments may be combined with each other and/or substituted for each other within the scope of this disclosure and appended claims.

Figure 1:
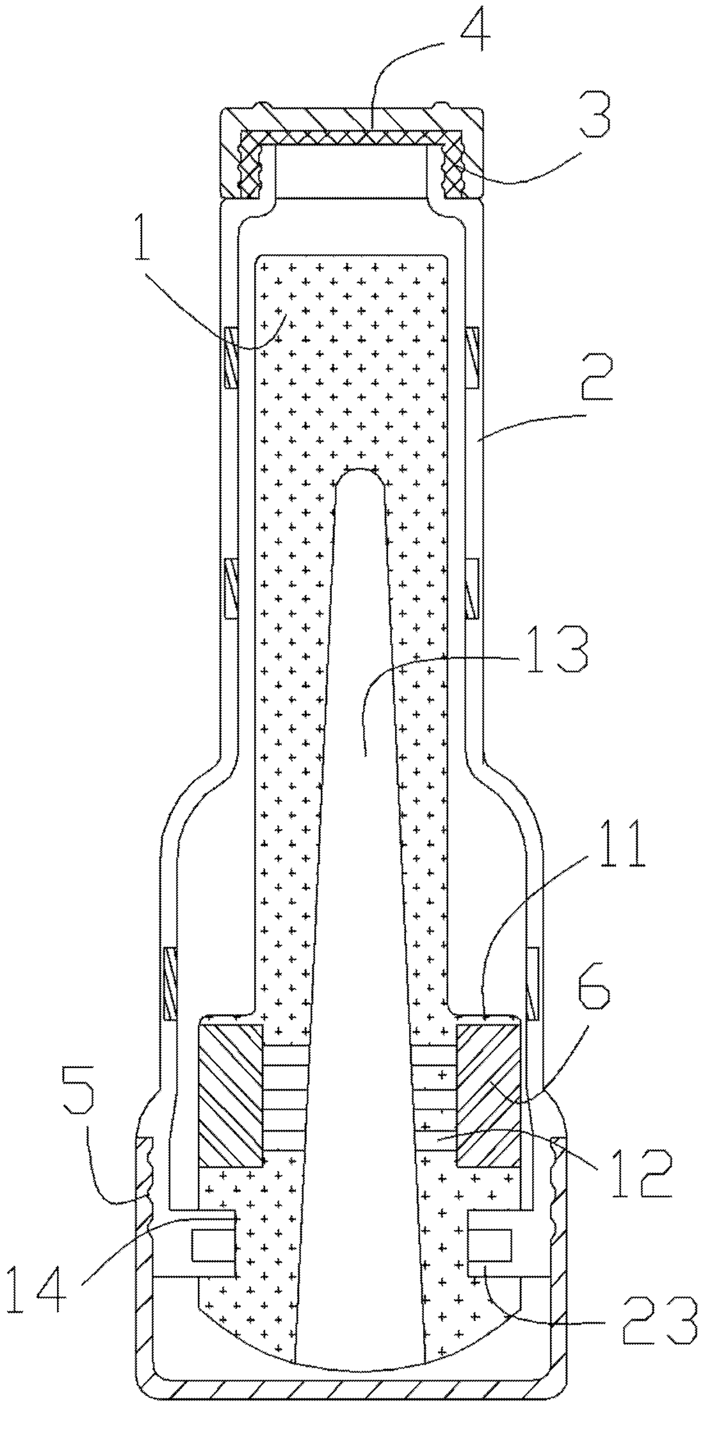
FIG. 1 is a cross sectional view of a device for treatment of premature ejaculation or stimulation of a male organ according to one embodiment disclosed in the present application.

FIG. 1 is a cross sectional view of a device for the treatment of premature ejaculation or stimulation of a male organ according to an embodiment disclosed in the present application. The device may include an elastic tube or sleeve 1 which can be removably mounted within a housing 2. According to the illustrated embodiment, the housing 2 may be generally in the shape of a flashlight with a generally cylindrical front section having a relatively large diameter and a generally cylindrical rear section having a relatively small diameter. It is appreciated that the housing 2 can be in any other appropriate shape so long as it can allow a user to easily hold the device by one or both hands.

The elastic sleeve 1 may have a generally tubular body and an enlarged head at a front open end thereof. The elastic sleeve 1 defines an elongated space 13 sized and shaped to receive therein a male organ, i.e. a penis of a male user. According to the illustrated embodiment, the elongated space 13 tapers from a front open end towards a rear closed end thereof. Although it is shown that the rear end is closed, it is contemplated that the rear end may be an open end as well. Although it is shown that the inner surface of the elastic surface 1 has a smooth profile, it is appreciated that the inner surface of the elastic sleeve 1 can be in any appropriate shape so long as it can be in contact with the male organ, and can stimulate the male organ when it is inserted into the elongated space 13 of the elastic sleeve 1 from the front open end thereof. The elastic sleeve 1 may be made of rubber, silicone, latex or any other suitable soft material that imitates the natural skin of a human being.

The surface of the front open end of the elastic sleeve 1 may be provided with an annular groove 14 for engagement with an annular projection 23 formed on an inner surface of the housing 2. This engagement allows the elastic sleeve 1 to be securely held within the housing 2 and limits axial movement of the elastic sleeve 1 relative to the housing 2 during use.

Figure 2:
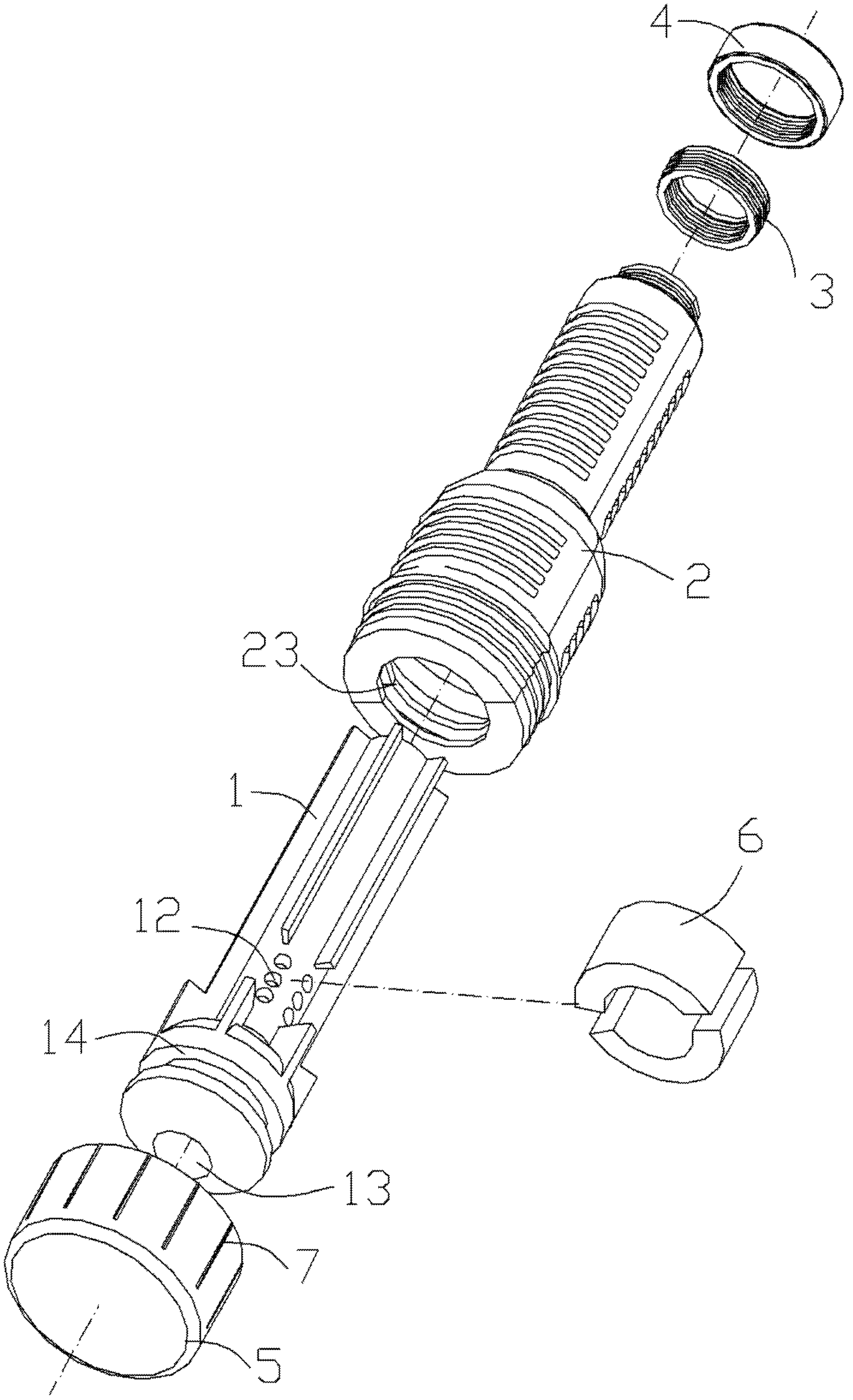
FIG. 2 is an exploded view of the device for treatment of premature ejaculation or stimulation of a male organ of FIG. 1.

One or more apertures 12 may be formed on the elastic sleeve 1. According to the embodiment shown in FIG. 2, there are six apertures 12 (2 rows and 3 columns) formed on one side of the elastic sleeve 1. The apertures 12 may be formed proximate to the front open end of the elastic sleeve 1 through which the male organ inserts. One or more apertures 12 may also be formed on the opposite side of the elastic sleeve 1. The apertures 12 may be disposed substantially around a section of the elastic sleeve 1 near the front open end thereof.

One or more liquid-absorbing members 6 can be held between the housing 2 and the elastic sleeve 1 over the apertures 12, as depicted in the cross sectional view of FIG. 1. One liquid-absorbing member 6 may be held between the housing 2 and one side of the elastic sleeve 1, and the other liquid-absorbing member 6 may be held between the housing 2 and an opposite side of the elastic sleeve 1. Each of the two liquid-absorbing members 6 may be generally semi-annular in shape, or in any other appropriate shape. The liquid-absorbing members 6 may be made of a foam material and formed into a piece of foam member, or any other possible liquid-absorbing member (e.g. a cotton pad) that can absorb a liquid and expel the liquid when squeezed.

The apertures 12 and the liquid-absorbing members 6 may be provided substantially around a front section of the elastic sleeve 1, and can be disposed inside the cylindrical front section of the housing 2 having a larger diameter. The liquid-absorbing members 6 are adapted to soak up at least one liquid and deliver the liquid through the apertures 12 and into the elastic sleeve 1 when the liquid-absorbing members 6 are squeezed by the male organ, which is being inserted into and frictionally moving to-and-fro inside the elastic sleeve 1.

Figure 7:
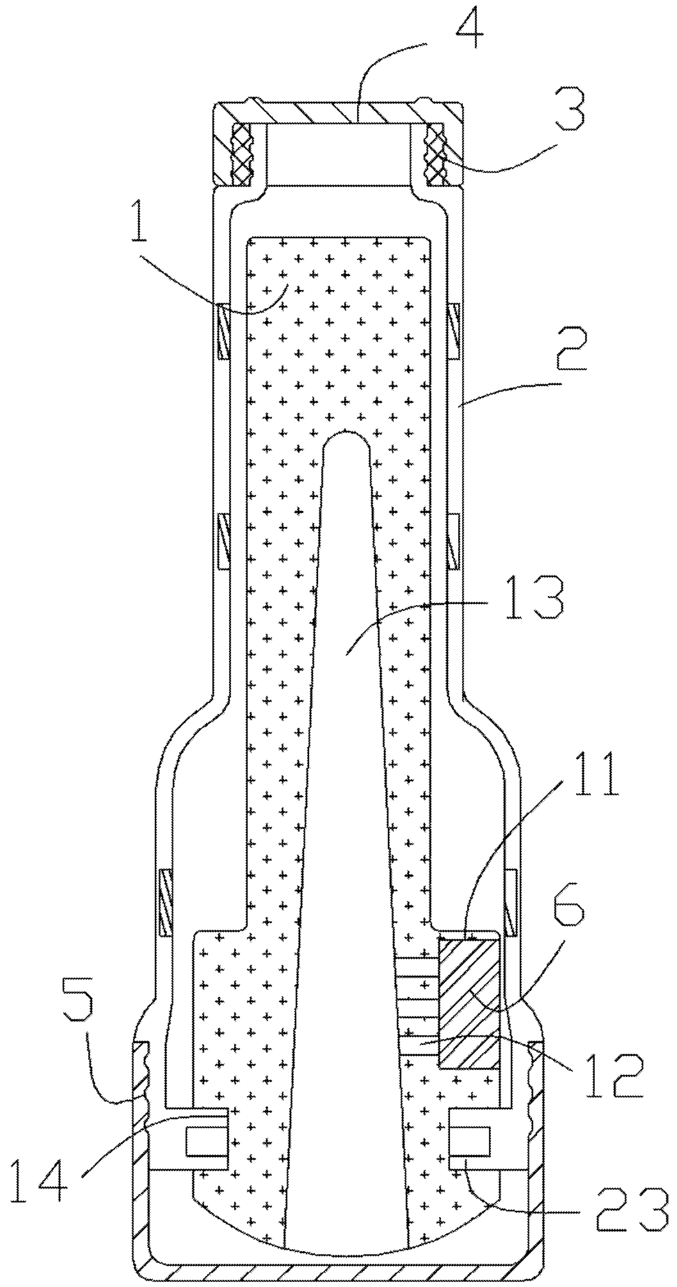
FIG. 7 is a cross sectional view of a device for treatment of premature ejaculation or stimulation of a male organ having only one liquid-absorbing member according to another embodiment disclosed in the present application.
Figure 8:
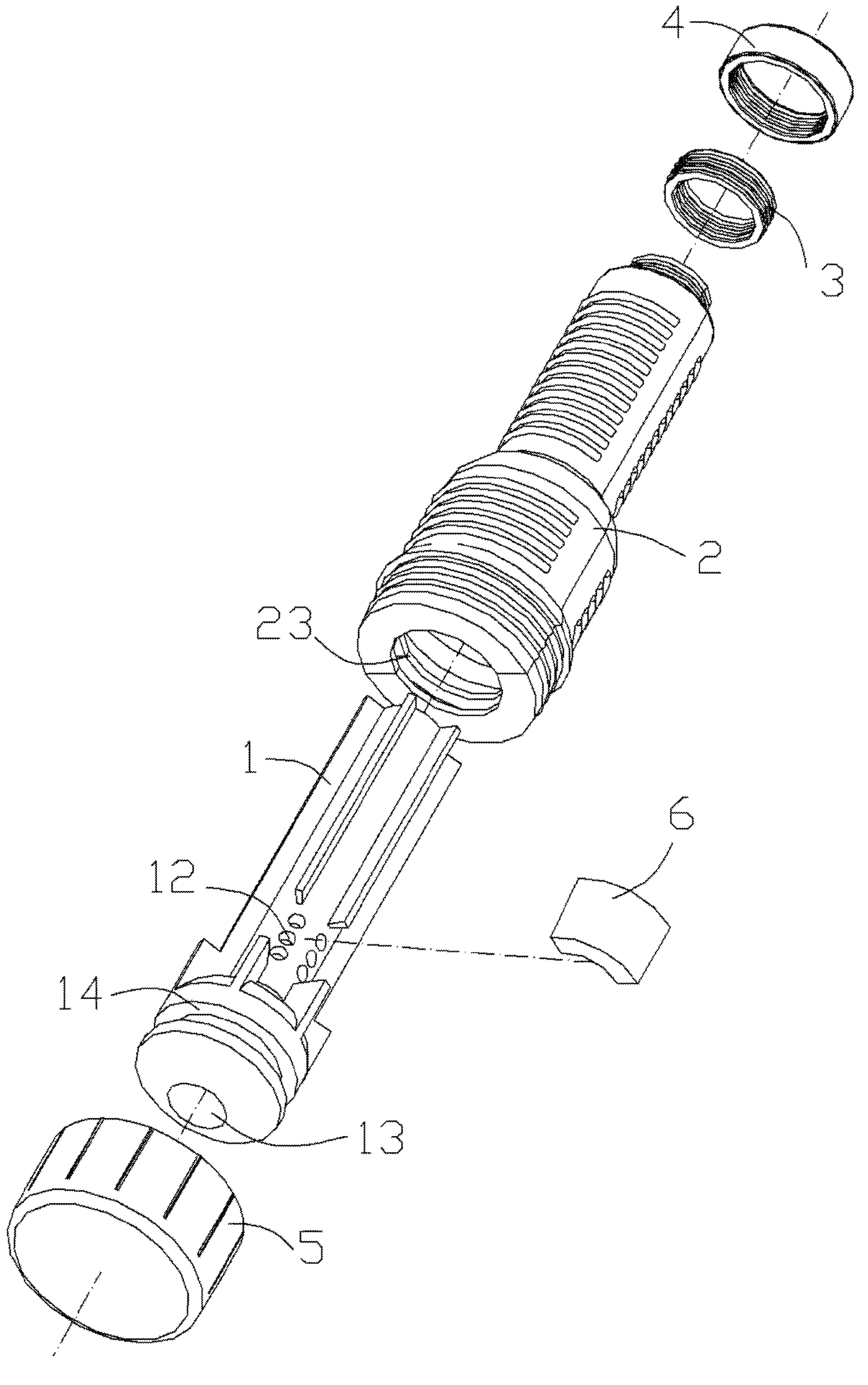
FIG. 8 is an exploded view of the device for treatment of premature ejaculation or stimulation of a male organ of FIG. 7.
Figure 9:
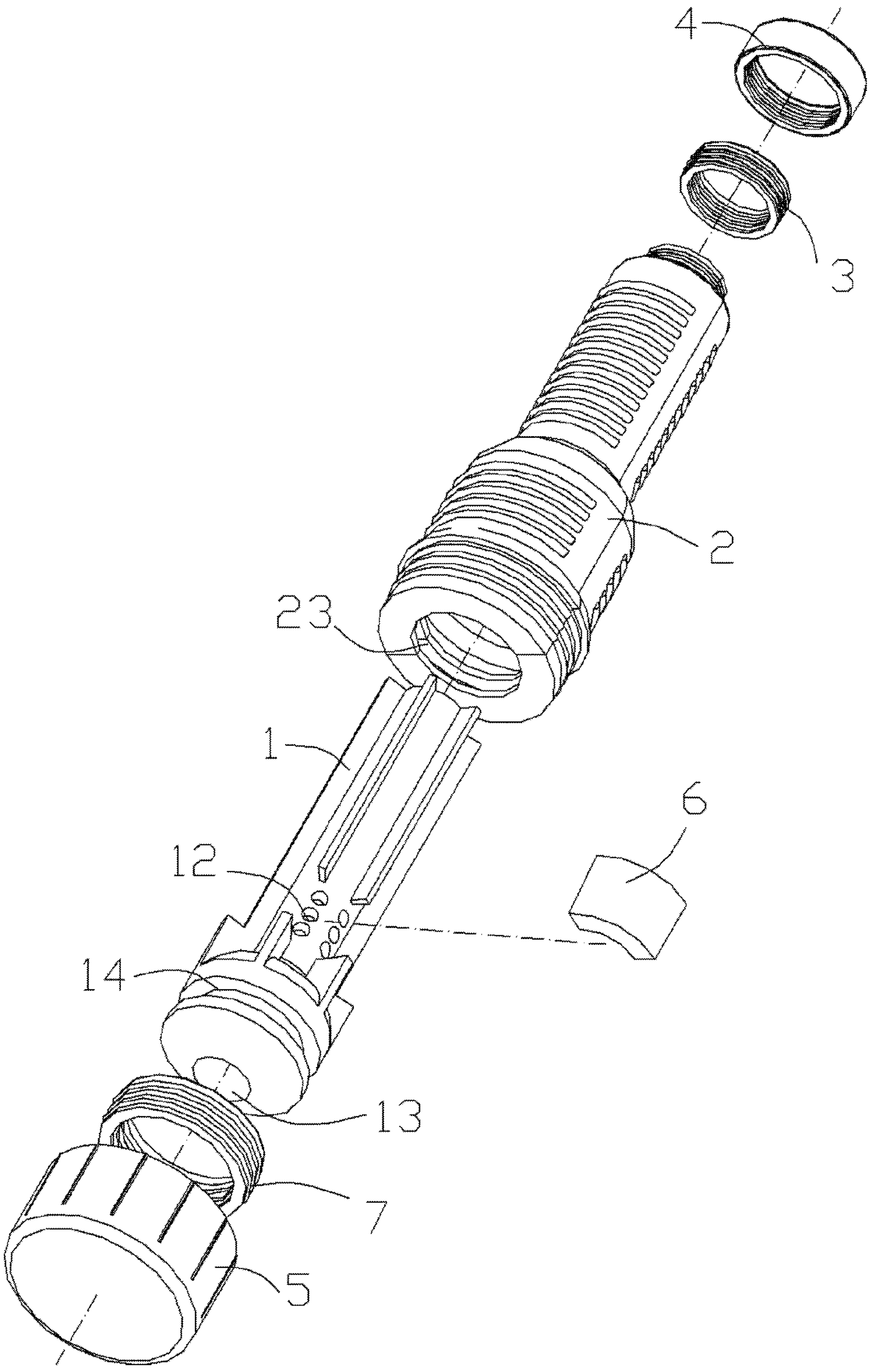
FIG. 9 is a similar exploded view of the device for treatment of premature ejaculation or stimulation of a male organ of FIG. 8, except that it has two fixing rings at both ends of the device instead of one fixing ring.

Although it has been shown and described that the device has two liquid-absorbing members 6 provided on one section of the elastic sleeve 1, it is understood that the device may have only one or more than two liquid-absorbing members 6, and the liquid-absorbing members 6 may be provided on more than one section of the elastic sleeve 1. FIGS. 7-9 show another embodiment of the device for treatment of premature ejaculation or stimulation of a male organ having only one liquid-absorbing member 6. According to this illustrated embodiment, the liquid-absorbing member 6 is generally quarter-annular in shape.

The liquid to be used in the device may be a lubricant, such as a lubricating oil. The lubricant may be a room-temperature lubricant, a warm/hot lubricant, or a cold/ice-cold lubricant. The liquid to be used in the device may also be water. The water may be room-temperature water, warm/hot water, or cold/ice-cold water. Details of the use of these liquids in cooperation with the device for treatment of premature ejaculation in the present application will be described in detail later.

The elastic sleeve 1 may be integrally formed with a plurality of elastic protrusions 11 extending outwardly from an outer surface of the elastic sleeve 1 for holding the liquid-absorbing members 6. The elastic protrusions 11 can define a space for receiving therein the liquid-absorbing members 6 in a position over the apertures 12. According to one embodiment shown in FIG. 2, the elastic protrusions 11 may be in the form of a plurality of ribs extending longitudinally along and spaced circumferentially about the elastic sleeve 1. The plurality of ribs may be formed with cut-out portions defining a space for holding therein the liquid-absorbing members 6. It is understood that the elastic protrusions 11 can be configured to hold the liquid-absorbing members 6 without the use of the housing 2 and the device can work without the housing 2.

Figure 3:
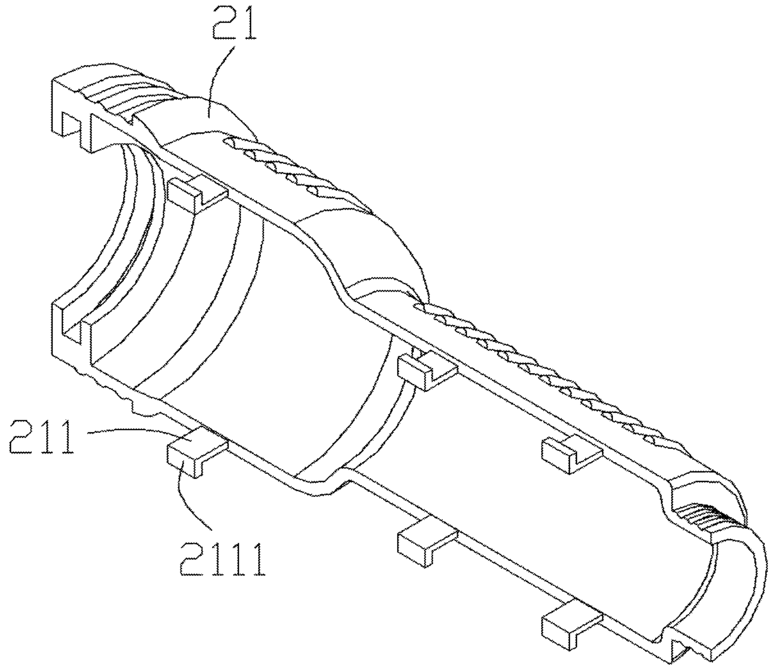
FIG. 3 is a perspective view of a first part of the housing of the device for treatment of premature ejaculation or stimulation of a male organ.
Figure 4:
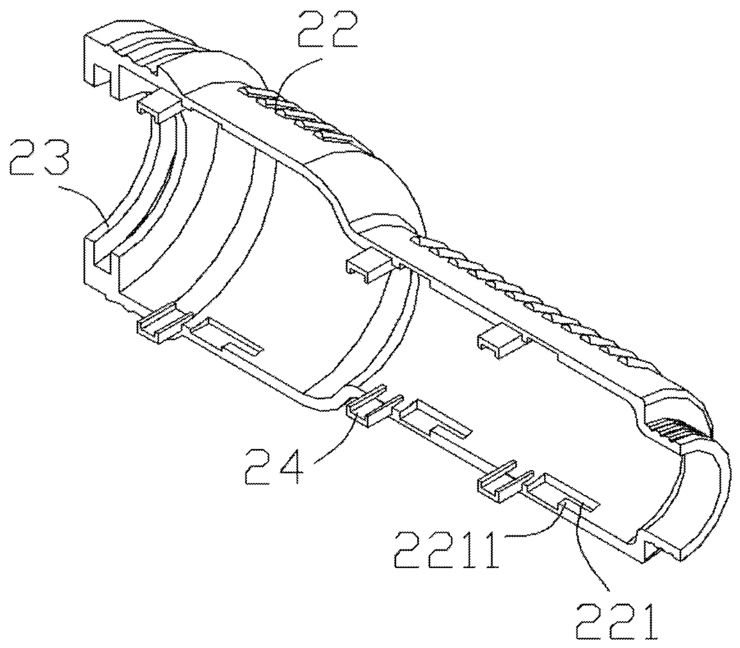
FIG. 4 is a perspective of a second part of the housing of the device for treatment of premature ejaculation or stimulation of a male organ.

The housing 2 of the device may include two separable housing parts. The two housing parts, or sections thereof, may be generally semi-cylindrical in shape. The two housing parts can be detachably fastened together by any suitable fastening means. According to one embodiment illustrated in FIGS. 3 and 4, fastening elements 211, 2111, 221, 2211 may be formed along the longitudinal edges of the two generally semi-cylindrical housing parts. The fastening elements 211, 2111, 221, 2211 may include a plurality of resilient latches 211 generally L-shape in cross section formed on the two longitudinal edges of one housing part, and a plurality of latch-retaining recesses 221 formed on the inner surfaces along the two longitudinal edges of the other housing part. Each L-shaped latch 211 may have a perpendicular latch portion 2111, and each latch-retaining recess 221 may have a side block portion 2211 for blocking the movement of the perpendicular latch portion 2111 thereby retaining the latch 211 in the latch-retaining recess 221 when engaged.

The housing 2 may be made of plastic or any other suitable material. The capability of separating the housing 2 into two housing parts permits a user to conveniently remove the elastic sleeve 1 from the housing 2, and remove the liquid-absorbing members 6 for soaking them up with liquid. It also allows a user to easily clean the elastic sleeve 1, the liquid-absorbing members 6 as well as the interior of the housing 2 of the device after use.

The device may further include a plurality of reinforcing extensions 24 extending from the two longitudinal edges of one housing part, and engageable with the inner surfaces of the other housing part when the two housing parts are fastened together by the fastening elements 211, 2111, 221, 2211. The reinforcing extensions 24 can be employed to reinforce the attachment of the housing parts by the fastening elements 211, 2111, 221, 2211. According to the illustrated embodiment, one reinforcing extension 24 is provided adjacent to each latch-retaining recess 221, and each reinforcing extension 24 has a cross section generally in the shape of a square bracket.

The device may further include two internally threaded end caps 4, 5 for closing the two opposite externally threaded open ends of the housing 2 respectively. Furthermore, two threaded fixing rings 3, 7 may be threadably engaged with and between each externally threaded open end and its corresponding internally threaded end cap 4, 5. The two threaded fixing rings 3, 7 can be employed to secure the threaded engagement of the two internally threaded end caps 4, 5 and the two opposite externally threaded open ends of the housing 2, and prevent leakage of liquid from the housing 2 during use. The two threaded end cap 4, 5 and the two threaded fixing rings 3, 7 may be made of plastic or any other suitable material.

The use of the device of the present application for treatment of premature ejaculation or stimulation of a male organ will now be described. To start a treatment of premature ejaculation or stimulation of a male organ using the device depicted in FIGS. 5 and 6, a user first opens the housing 2 by unscrewing the two end caps 4, 5, and then unscrewing the two rings 3, 7 from the two opposite ends of the housing 2. After the end caps 4, 5 and the rings 3, 7 are removed, the two housing parts of the housing 2 can be separated. The two liquid-absorbing members 6 are soaked with a lubricant. The lubricant may be in room temperature, or may be heated up to a relatively warm/hot temperature, or cold down to a relatively cold/ice cold temperature as compared to the normal body temperature of the user. To soak the liquid-absorbing members 6 with a lubricant, one can either slowly pour the lubricant directly onto the liquid-absorbing members 6, or remove the liquid-absorbing members 6 and then soak them into a bottle filled with lubricant. After the liquid-absorbing members 6 are fully soaked up with lubricant, the two housing parts of the housing 2 are then attached together by coupling the resilient latches 211, 2111 of one housing part to the corresponding latch-retaining recesses 221, 2211 of the other housing part. The rings 3, 7 and the end caps 4, 5 are then screwed back to their respective ends of the housing 2.

The user then inserts his male organ into the elongated space 13 of the elastic sleeve 1 through the front open end thereof and moves the male organ to-and-fro inside the elastic sleeve 1. When the male organ is inserting into the elastic sleeve 1 and frictionally moving to-and-fro inside the elastic sleeve 1, it presses against the two lubricant-soaked members 6 thereby squeezing the lubricant out of the lubricant-soaked members 6, through the apertures 12 on the two opposite sides of the elastic sleeve 1, and into the elongated space 13 where it comes into contact with the male organ. As shown in FIG. 1, the elongated space 13 may be tapering from the front open end towards the rear closing end of the elastic sleeve 1. Since the sleeve 1 is elastic and stretchable, the male organ can be in close contact with the inner surface of the elastic sleeve 1 when the male organ is moving to-and-fro inside the elastic sleeve 1. The touch receptors in the skin of the male organ can sense the touch of the elastic sleeve 1 and the male organ can be stimulated. It is appreciated that the head of the male organ can be the most stimulated portion of the male organ.

Furthermore, hot or cold lubricant entering the elongated space 13 through the apertures 12 can further stimulate the male organ. Hot receptors in the skin of the male organ start to perceive hot sensation when the temperature of the lubricant at the surface of the skin is above the temperature of the male organ. Similarly, cold receptors in the skin of the male organ start to perceive cold sensation when the temperature of the lubricant at the surface of the skin is below the temperature of the male organ. This penile stimulation can decrease the sensitivity of the male organ in particular the head thereof, and can serve as a treatment of premature ejaculation.

Although it has been shown and described that the elongated space 13 has a smooth tapering profile, it is understood that the inner surface of the elastic sleeve 1 can be provided with a non-smooth profile such as generally wavy surfaces, or a plurality of inwardly projecting nubs and ribs integrally formed along the elastic sleeve 1 for massaging and further stimulating the male organ.

Figure 5:
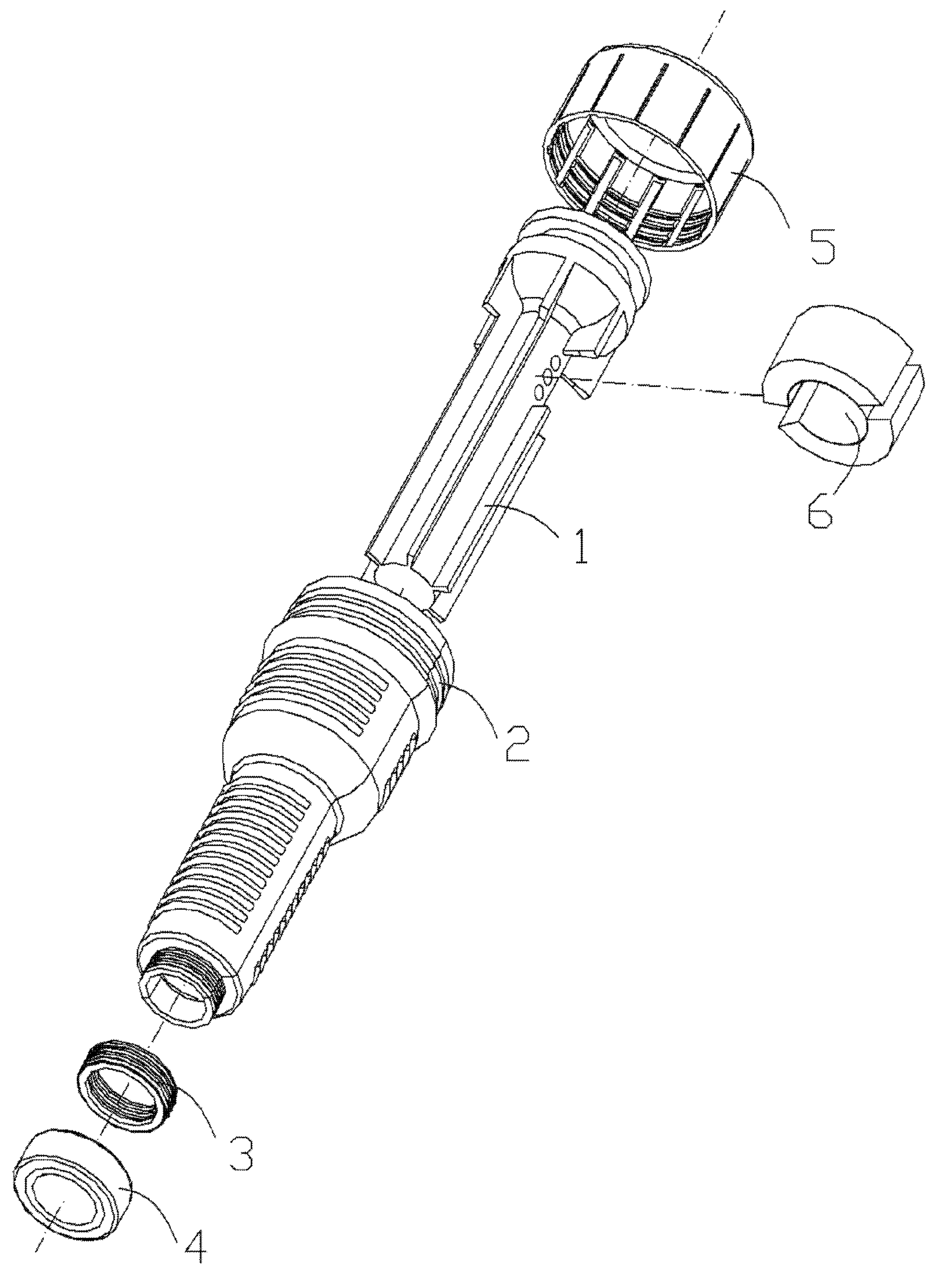
FIG. 5 is an exploded view of the device for treatment of premature ejaculation or stimulation of a male organ according to another embodiment in the present application.
Figure 6:
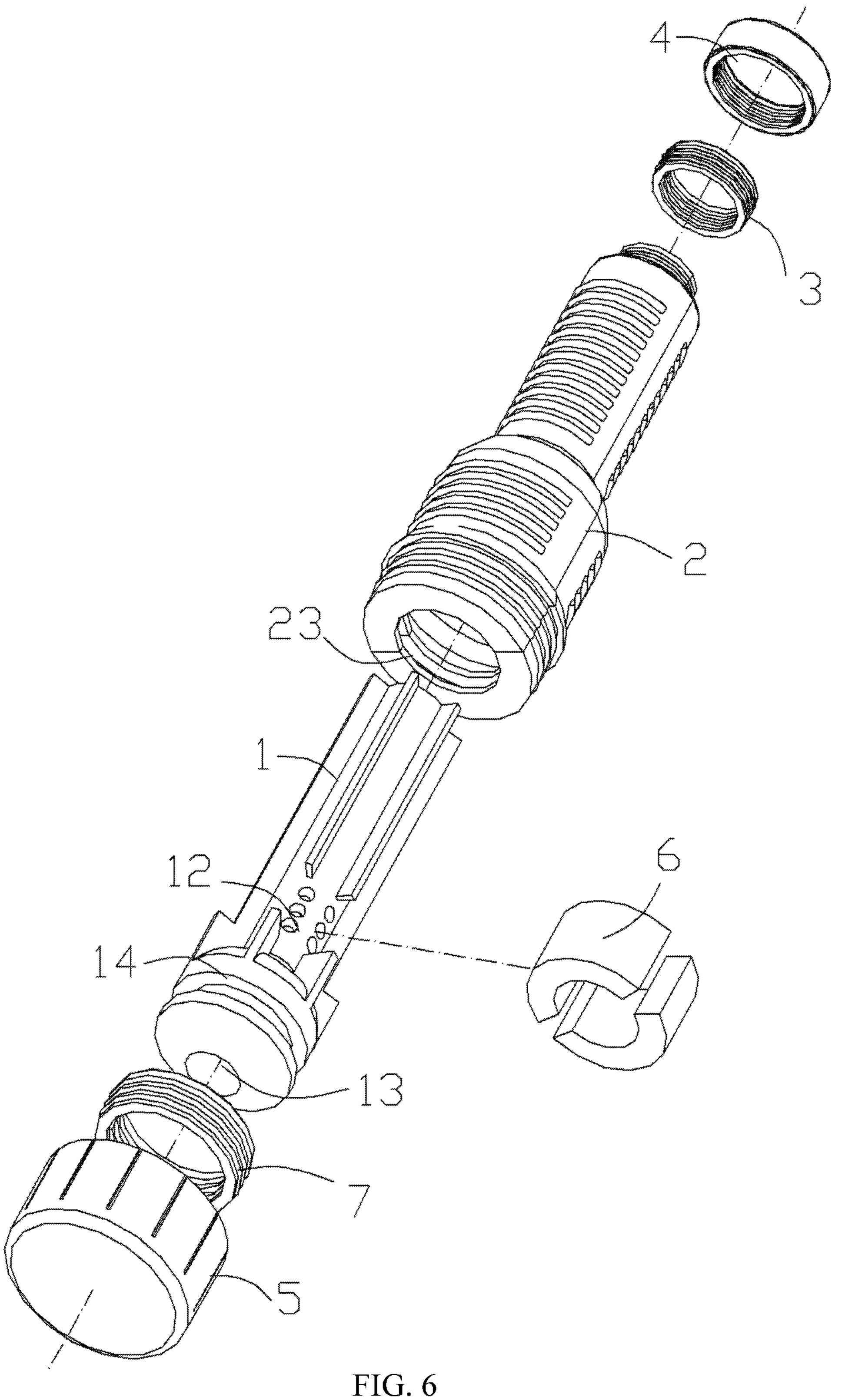
FIG. 6 is another exploded view of the device for treatment of premature ejaculation or stimulation of a male organ in FIG. 5.

To start another treatment of premature ejaculation or another way of stimulation of a male organ using the device in FIGS. 5 and 6, a user first opens the housing 2. Instead of lubricant, the two liquid-absorbing members 6 are soaked with water. The two liquid-absorbing members 6 may be soaked with warm/hot water having a relatively warm/hot temperature as compared to the normal body temperature of the user. The two liquid-absorbing members 6 may also be soaked with cold/ice-cold water having a relatively cold/ice-cold temperature as compared to the normal body temperature of the user.

Similarly, to soak the two liquid-absorbing members 6 with water, one can either slowly pour the water directly onto the two liquid-absorbing members 6, or remove the two liquid-absorbing members 6 from the housing 2 and then soak them into a bottle filled with water. After the two liquid-absorbing members 6 are fully soaked up with warm/hot or cold/ice-cold water, the two housing parts of the housing 2 are then attached together by the fastening elements 211, 2111, 221, 2211. The rings 3, 7 and the end caps 4, 5 are then screwed back to their respective ends of the housing 2.

The user then inserts his male organ into the elongated space 13 of the elastic sleeve 1 through the front open end thereof and moves the male organ to-and-fro inside the elastic sleeve 1. When the male organ is inserting into the elastic sleeve 1 and frictionally moving to-and-fro inside the elastic sleeve 1, it presses against the two water-soaked members 6 thereby squeezing the warm/hot or cold/ice-cold water out of the water-soaked members 6, through the apertures 12 on the two opposite sides of the elastic sleeve 1, and into the elongated space 13 where it comes into contact with the male organ.

Similar to warm/hot or cold/ice-cold lubricant, warm/hot and cold/ice-cold water can stimulate the male organ. Hot receptors in the skin of the male organ start to perceive warm/hot sensation when the temperature of warm/hot water at the surface of the skin is above the temperature of the male organ. Similarly, cold receptors in the skin of the male organ start to perceive cold/ice-cold sensation when the temperature of cold/ice-cold water at the surface of the skin is below the temperature of the male organ. These penile stimulation can decrease the sensitivity of the male organ, in particular the head thereof, and can serve as a treatment of premature ejaculation.

To start a further treatment of premature ejaculation or a further way of stimulation of a male organ using the device in FIGS. 5 and 6, the user soaks one liquid-absorbing member 6 at one side of the elastic sleeve 1 with warm/hot lubricant or water having a relatively warm/hot temperature as compared to the normal body temperature of the user; and soaks the other liquid-absorbing member 6 at the opposite side of the elastic sleeve 1 with cold/ice-cold lubricant or water having a relatively cold/ice-cold temperature as compared to the normal body temperature of the user.

The user then inserts his male organ into the elongated space 13 of the elastic sleeve 1 through the front open end thereof and moves the male organ to-and-fro inside the elastic sleeve 1. When the male organ is inserting into the elastic sleeve 1 and frictionally moving to-and-fro inside the elastic sleeve 1, it (i) presses against the liquid-absorbing member 6 soaked with warm/hot lubricant or water, thereby squeezing the warm/hot lubricant or water out of the liquid-absorbing member 6, through the apertures 12 at one side of the elastic sleeve 1, and into the elongated space 13 where it comes into contact with one side of the male organ; and (ii) at the same time presses against the other liquid-absorbing member 6 soaked with cold/ice-cold lubricant or water, thereby squeezing the cold/ice-cold lubricant or water out of the other liquid-absorbing member 6, through the apertures 12 at the opposite side of the elastic sleeve 1, and into the elongated space 13 where it comes into contact with the other side of the male organ. The effect is that one side of the male organ is stimulated by warm/hot lubricant or water, and the other side of the male organ is stimulated by cold/ice-cold lubricant or water. Furthermore, the user may rotate the device relative to the male organ. If the device is rotated clockwise or anticlockwise 180 degrees, then the one side of the male organ initially stimulated by warm/hot lubricant or water will now be stimulated by cold/ice-cold lubricant or water; and the other side of the male organ initially stimulated by cold/ice-cold lubricant or water will now be stimulated by warm/hot lubricant or water. This alternation of warm/hot and cold/ice-cold lubricant or water can further stimulate the male organ and decrease the sensitivity of the male organ, in particular the head thereof, and can serve as a treatment of premature ejaculation.

The device for treatment of premature ejaculation of the present application can be used as a male masturbator for stimulating the male organ, and stimulation of a male organ can treat premature ejaculation. When the device is used as a male masturbator for stimulating the male organ, the front open end of the elastic sleeve 1 may be molded into the shape of a female vagina in order to stimulate the male user during masturbation.

While the device for treatment of premature ejaculation or stimulation of a male organ disclosed in the present application has been shown and described with particular references to a number of preferred embodiments thereof, it should be noted that various other changes or modifications may be made without departing from the scope of the appending claims.

What is claimed is:

1. A device for treatment of premature ejaculation or stimulation of a male organ comprising:

(a) a housing;

(b) an elastic sleeve mounted within the housing and defining an elongated space;

(c) at least one aperture formed on the elastic sleeve and configured to allow a liquid outside the elongated space and with a temperature higher or lower than a body temperature of a user to flow into the elongated space of the elastic sleeve; and (d) at least one liquid-absorbing member held between the housing and the elastic sleeve over the at least one aperture; wherein the at least one liquid-absorbing member is placed over and around the at least one aperture to completely cover the at least one aperture;

(e) wherein the at least one liquid-absorbing member is configured to soak up the liquid and deliver the liquid through the at least one aperture and into the elongated space of the elastic sleeve when the at least one liquid-absorbing member is squeezed.

2. The device as claimed in claim 1, wherein the at least one liquid-absorbing member is a foam member.

3. The device as claimed in claim 1, comprising a first plurality of apertures formed at one side of the elastic sleeve, and a second plurality of apertures formed at an opposite side of the elastic sleeve.

4. The device as claimed in claim 1, wherein an outer surface of the elastic sleeve is integrally formed with a plurality of ribs extending longitudinally along and spaced circumferentially about the elastic sleeve, and the plurality of ribs is formed with cut-out portions defining a space for holding therein the at least one liquid-absorbing member.

5. The device as claimed in claim 1, comprising two liquid-absorbing members, wherein one liquid-absorbing member is held between the housing and one side of the elastic sleeve and is soaked with a warm/hot liquid, and the other liquid-absorbing member is held between the housing and an opposite side of the elastic sleeve and is soaked with a cold/ice-cold liquid, whereby rotation of the housing around the male organ 180 degrees clockwise or anticlockwise stimulates the male organ by alternate warm/hot and cold/ice-cold liquid.

6. The device as claimed in claim 1, wherein the housing comprises two substantially semi-cylindrical housing parts detachably fastened together by fastening elements formed along longitudinal edges of the two housing parts.

7. The device as claimed in claim 6, wherein the fastening elements comprise a plurality of resilient latches of generally L-shape cross section formed on the longitudinal edges of one of the two housing parts, and a plurality of latch-retaining recesses formed on inner surfaces of the longitudinal edges of the other one of the two housing parts for engagement with the latches respectively.

8. The device as claimed in claim 6, wherein the at least one liquid-absorbing member is generally semi-annular or quarter-annular in shape.

9. The device as claimed in claim 6, further comprising a plurality of reinforcing extensions extending from the longitudinal edges of one of the two housing parts, and engageable with a plurality of inner surfaces along the longitudinal edges of the other one of the two housing parts respectively when the two housing parts are fastened together by the fastening elements.

10. The device as claimed in claim 6, further comprising two internally threaded end caps for closing two opposite externally threaded open ends of the housing respectively.

11. The device as claimed in claim 10, further comprising a threaded ring threadably engaged with and between each externally threaded open end of the housing and its corresponding internally threaded end cap.

12. A device for treatment of premature ejaculation or stimulation of a male organ comprising:

(a) an elastic sleeve defining an elongated space;

(b) at least one aperture formed on the elastic sleeve and configured to allow a liquid outside the elongated space and_with a temperature higher or lower than a body temperature of a user to flow into the elongated space of the elastic sleeve; and (c) at least one liquid-absorbing member held over the at least one aperture; wherein the at least one liquid-absorbing member is placed over and around the at least one aperture to completely cover the at least one aperture;

(d) wherein the at least one liquid-absorbing member is configured to soak up the liquid and deliver the liquid through the at least one aperture and into the elongated space of the elastic sleeve when the at least one liquid-absorbing member is squeezed.

13. The device as claimed in claim 12, wherein the at least one liquid-absorbing member is a foam member.

14. The device as claimed in claim 12, comprising a first plurality of apertures formed at one side of the elastic sleeve, and a second plurality of apertures formed at an opposite side of the elastic sleeve.

15. The device as claimed in claim 12, wherein an outer surface of the elastic sleeve is integrally formed with a plurality of ribs extending longitudinally along and spaced circumferentially about the elastic sleeve, and the plurality of ribs is formed with cut-out portions defining a space for holding therein the at least one liquid-absorbing member.

16. The device as claimed in claim 12, comprising two liquid-absorbing members, wherein one liquid-absorbing member is held at one side of the elastic sleeve and is soaked with a warm/hot liquid, and the other liquid-absorbing member is held at an opposite side of the elastic sleeve and is soaked with a cold/ice-cold liquid.

17. The device as claimed in claim 12, wherein the at least one liquid-absorbing member is generally semi-annular or quarter-annular in shape.

* * * * *